United States Patent [19]
Masini

[11] Patent Number: 5,643,189
[45] Date of Patent: Jul. 1, 1997

[54] COMPOSITE WOUND DRESSING INCLUDING INVERSION MEANS

[76] Inventor: Michael A. Masini, 4817 Hillway Ct., Ann Arbor, Mich. 48105

[21] Appl. No.: 350,822

[22] Filed: Dec. 7, 1994

[51] Int. Cl.[6] ................................................. A61F 13/00
[52] U.S. Cl. .................. 602/58; 602/45; 602/57; 604/385.1; 604/307; 206/440
[58] Field of Search ........................ 604/304, 307, 604/385.1; 606/151, 213; 602/42, 57, 58, 59, 78, 79, 44, 45, 54; 206/440

[56] References Cited

U.S. PATENT DOCUMENTS

| | | | |
|---|---|---|---|
| 3,521,631 | 7/1970 | Gardner | 602/42 X |
| 4,085,753 | 4/1978 | Gellert | 604/385.1 |
| 4,182,336 | 1/1980 | Black | 128/290 |
| 4,212,296 | 7/1980 | Schaar | 602/42 X |
| 4,341,208 | 7/1982 | Gordon | 604/307 X |
| 4,430,087 | 2/1984 | Azpiri | 604/385 |
| 4,545,372 | 10/1985 | Lauritzen | 128/156 |
| 4,802,884 | 2/1989 | Fröiah et al. | 493/339 |
| 4,808,175 | 2/1989 | Hansen | 640/385.1 |
| 4,923,455 | 5/1990 | Dean | 604/385.1 |
| 4,964,857 | 10/1990 | Osborn | 604/395 |
| 4,964,859 | 10/1990 | Feldman | 604/385.1 |
| 5,037,414 | 8/1991 | Booth | 604/385.1 |
| 5,086,763 | 2/1992 | Hathman | 602/42 |
| 5,170,781 | 12/1992 | Loomis | 602/42 X |
| 5,193,684 | 3/1993 | McDonald | 206/581 |
| 5,196,244 | 3/1993 | Beck | 428/35.2 |
| 5,259,503 | 11/1993 | Steingraber, Jr. | 206/440 |
| 5,301,806 | 4/1994 | Olson | 206/278 |

*Primary Examiner*—Michael Powell Buiz
*Assistant Examiner*—Chalin Smith
*Attorney, Agent, or Firm*—Gifford, Krass, Groh, Sprinkle, Patmore, Anderson & Citkowski

[57] ABSTRACT

A hospital type of bandage integrates an absorbent pad and non-stick layer with a fluid-impermeable outer layer and an adhesive in a single composite structure. In a preferred embodiment the invention further includes means which may be used to turn the bandage inside out upon removal, so that surfaces once contacting a patient are no longer externally exposed. A bandage according to the invertible embodiment preferably includes a pocket formed on the side of the bandage facing away from the patient after application, this pocket being large enough to accommodate at least a portion of a human hand, and inside this pocket and located opposite the entrance is a means for grasping which may be pulled outwardly through pocket opening, thereby inverting the entire structure. Various forms of devices for grasping are possible as alternatives, including a string, a tab and a tab with one or more finger-receiving holes. Means are further included for sealing the inverted structure, preferably in the form of a flap and associated adhesive.

13 Claims, 5 Drawing Sheets

COMPOSITE WOUND DRESSING INCLUDING INVERSION MEANS

FIELD OF THE INVENTION

The present invention relates generally to larger bandages of the type used, for example, in hospital settings and, more particularly, to a composite bandage with integrated absorbent, adhesive and fluid-impermeable layers. In a preferred embodiment the bandage may further be turned inside-out to self-contain surfaces once exposed to the patient.

BACKGROUND OF THE INVENTION

The AIDS epidemic, in particular, has caused medical personnel to take extreme precautions to avoid exposure to blood and other bodily fluids which might be infected. Doctors and dentists now wear rubber gloves and face masks in even the most routine situations, and various safety devices such as protective needles and so forth are being introduced with increasing frequency.

The removal of bandages and other wound dressings is an area where further safety measures are warranted. There are no composite wound dressings which integrate adhesive and absorbent layers in combination with a fluid impermeable cover. Instead, physicians routinely open a first sterilized pouch containing an absorbent pad and place that on the wound. Then rolls of sterilized tape are opened and, quite often, not only are the edges of the absorbent pad taped to the patient, but excessive tape is often used to cover the entire pad outer surface to ensure a fluid-tight seal. This is time consuming, and also results in multiple items requiring independent sterilization and considerable packaging waste.

The used bandages are discarded by placing them into specially marked bags which, in turn, are placed in specially marked disposal containers. This practice may expose associated personnel to dangerous pathogens since until such dressings are placed in their specially marked disposal containers, the surfaces once applied to the patient are outwardly unprotected. Also, there exists no consistent technique for placement within such bags, which may lead to contact with personnel during the process of insertion into the disposal bag or container.

SUMMARY OF THE INVENTION

The present invention solves problems associated with the application and disposal of wound dressings by providing a bandage which integrates an absorbent pad having a non-stick layer with a fluid-impermeable outer layer and adhesive in a single composite structure, so that only one item need be sterilized and accounted for. In a preferred embodiment, the invention further includes means which may be used to turn the bandage inside-out upon removal, so that surfaces once contacting a patient are no longer externally exposed. In this way, the bandage itself forms its own disposal pouch, thus solving the above-mentioned problems, including possible exposure during bandage removal and transfer, and further obviates the necessity for separate sterilized disposal vehicles.

In the invertible embodiment, a bandage according to the invention preferably includes a pocket formed on the side of the bandage facing away from the patient after application, this pocket being large enough to accommodate at least a portion of a human hand, preferably the entire hand. Inside this pocket and located opposite the entrance to the pocket is a graspable device which may be pulled outwardly through the pocket opening, thereby inverting the entire structure. Various forms of grasping means are possible as alternatives, including a string, a tab and a tab including one or more finger-receiving holes. Means are further included for sealing the bag once it is inverted, preferably in the form of a flap and associated adhesive. In the preferred embodiment this flap is also stiffened to be conveniently held by the hand not performing the actual inversion, with the two hands then cooperating for a smooth motion as the bandage structure is turned inside out. Other sealing means may be provided as alternatives, however, such as adhesive tape, a zip-lock type of fastener, or one or more semi-rigid but flexible cooperating elements disposed proximate to the pocket opening.

The semi-rigid or rigid flap is preferably folded near the mouth of the pocket prior to inversion so as to provide a stiffening proximate to the mouth of the pocket to help maintain structural integrity during inversion. The bandage may also include other, additional means to stiffen the mouth of the pocket opening and may further include some form of holding member extending outwardly from the side of the bandage at a point near to the entrance to the pocket, preferably in the form of a rigid or semi-rigid bar or stick-like protrusion which may be held by one hand while the bandage is inverted with the other. The protrusion may further be hingedly affixed to the side of the bandage to form a more compact structure until it is employed, and may fold over and seal the entrance to the pocket following inversion.

DETAILED DESCRIPTION OF THE INVENTION

Figure 1A:
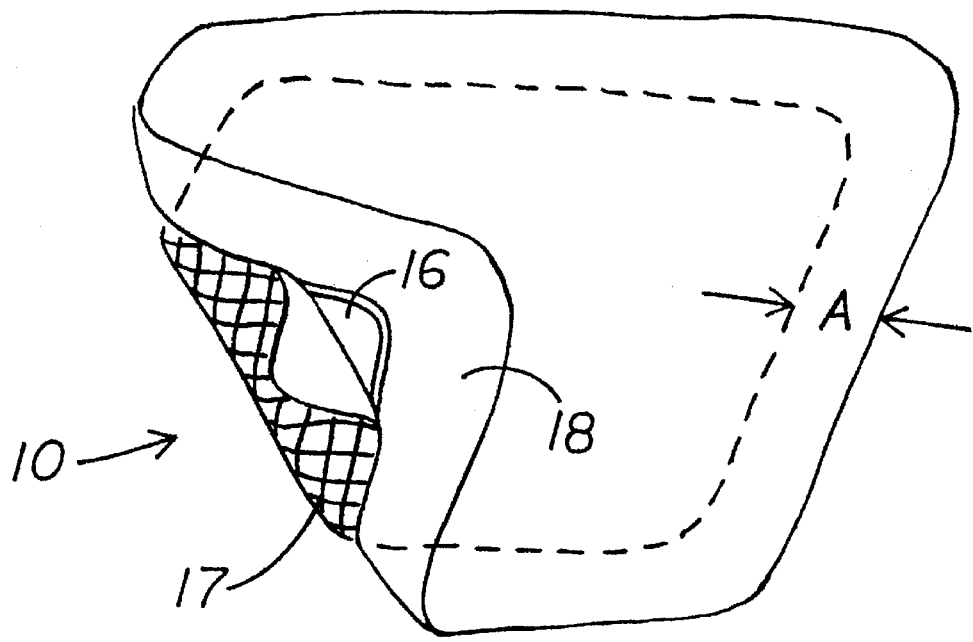
FIG. 1A is an oblique drawing of a bandage formed in accordance with this invention, with an area being folded over to show its absorbent and adhesive portions.

The present invention is directed toward bandages such as surgical dressings large enough to be used in post-operative situations, for example. Thus, bandages according to the invention range in size from a couple inches or so per side up to several inches per side, and are preferably rectangular in shape, in contrast to the small bandages and adhesive strips used for minor cuts and bruises. FIG. 1A shows at 10 a basic embodiment of a bandage formed according to the invention including an absorbent layer or pad 16 with non-stick layer 17 attached to a larger, fluid-impermeable layer 18. The layer 18 preferably extends beyond the pad 16 around its entire periphery by an amount depicted as "A," with at least a portion of this outwardly extending region of layer 18 including an adhesive at least between the pad and the outer edge of the layer 18 for securement to the patient.

In a preferred construction, a single fluid-impermeable layer 18 is provided with a relatively strong adhesive across the entirety of one of its two surfaces, which is used to hold the pad 16 to that surface with the remaining exposed peripheral portions with adhesive being used for patient contacting. Alternatively, further layers may be provided, such as a separate adhesive layer and fluid-impermeable layer. Although the figure shows substantially the same width of "A" around the entire periphery of the pad 16 and round corners, variations of these geometrical considerations are possible, as is non-rectangular overall shapes, such as ovals and circles, and so forth.

Preferably, the absorbent wound-contacting pad 16 includes a non-stick outer surface such as an Adaptic™-type layer (shown with hashed markings), which is popular in the profession since fluids may pass therethrough, but with the outer surface not adhering to the patient or wound. Also, in the preferred construction, at least the adhesive exposed for securement to the patient is preferably of the Microfoam type, as this is sufficiently strong enough to provide a good bond to the skin, but which is also flexible and tends to roll off the skin when lifted and pulled laterally, a feature which is advantageous for the invertible version of the bandage, as should be evident as discussed below. As with the variations possible in geometrical shape, variations in the use of the absorbent, adhesive and fluid-impermeable materials are also possible.

Figure 1B:
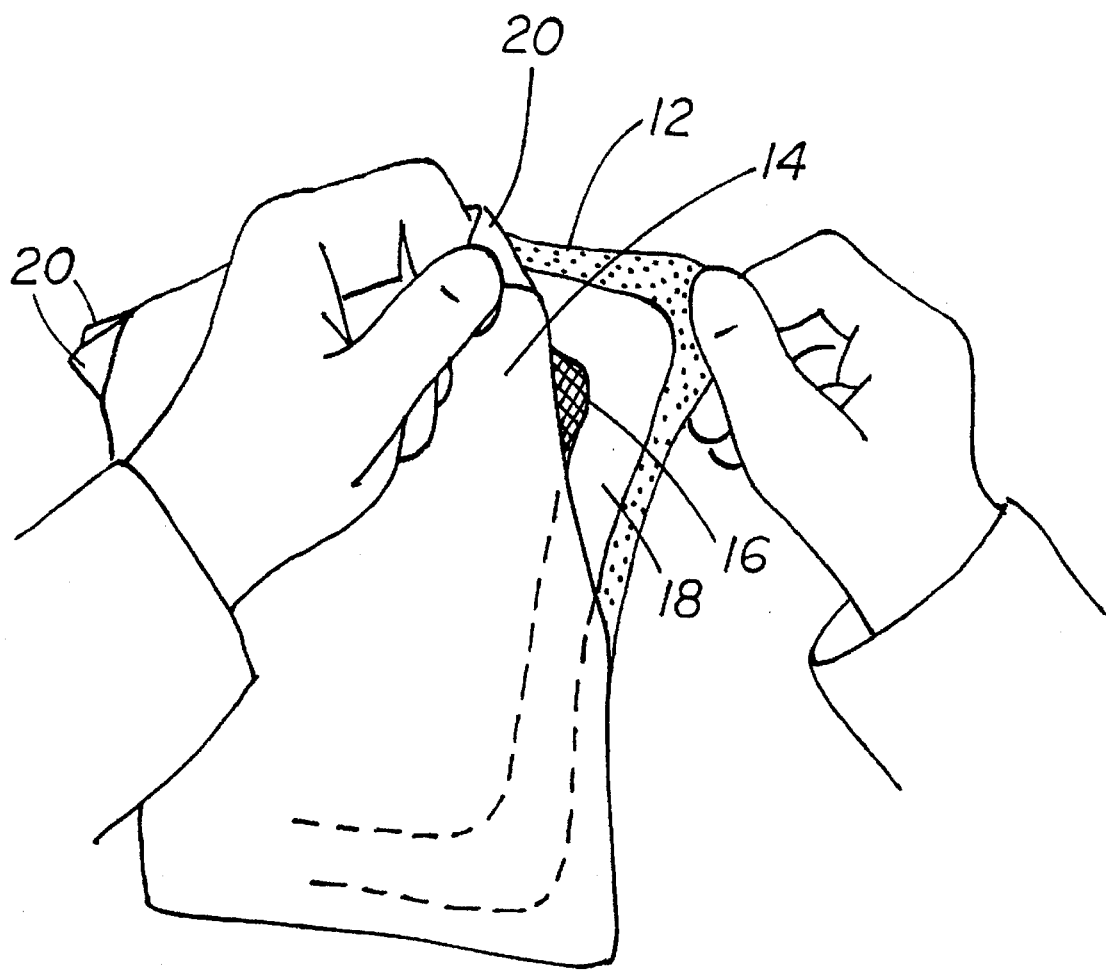
FIG. 1B is an oblique drawing illustrating a preferred form of packaging for a bandage constructed according to the invention.

FIG. 1B shows a preferred delivery method of the bandage of FIG. 1A, wherein two outer sheets 12 and 14 are used to entirely contain the bandage, and are accordingly the only materials that need to be discarded upon application. As shown in FIG. 1B, these outer layers 12 and 14, which may be of paper, foil, plastic or other alternative materials, are preferably slightly larger than the bandage itself and are sealed together beyond the extent of the bandage with an adhesive shown by the stippling, which releases as the two halves 12 and 14 are pulled apart as shown. The surface of the layer 14 facing the exposed adhesive portions of the bandage of layer 18 may further include a non-stick type of surface to ensure that the bandage does not stick to the packaging layer so as to cause problems upon removal. Dog-ear tabs 20 may further optionally be provided as a convenient grasping means for pulling apart the layers 12 and 14 during removal of the bandage 10.

Figure 2A:
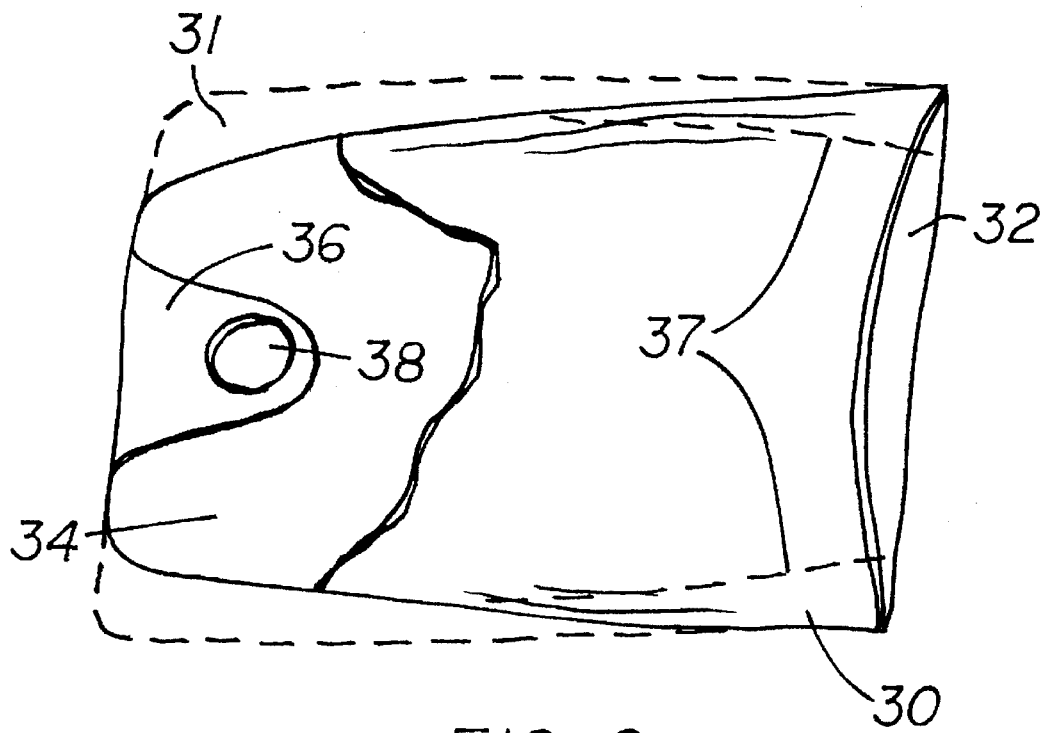
FIG. 2A is an oblique drawing of an invertible version of the bandage, with a portion of the outer layer being removed to expose a pull tab.
Figure 2B:
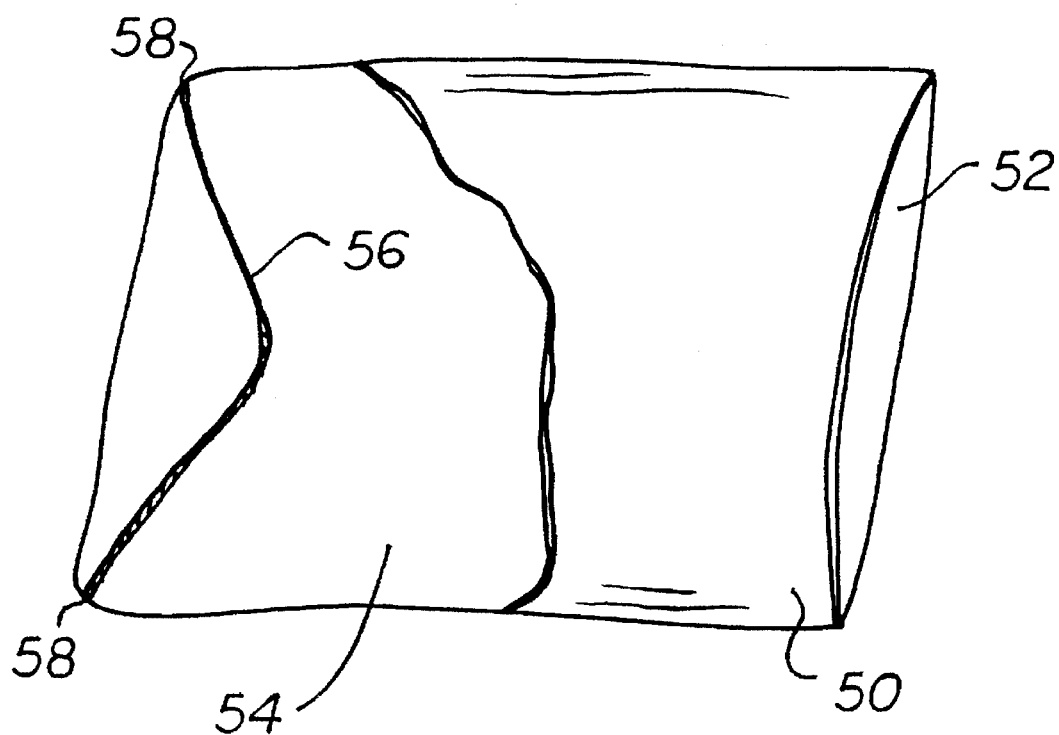
FIG. 2B is an oblique drawing of an invertible version of the bandage, with a portion of the outer layer being removed to show a string used for inversion.
Figure 2C:
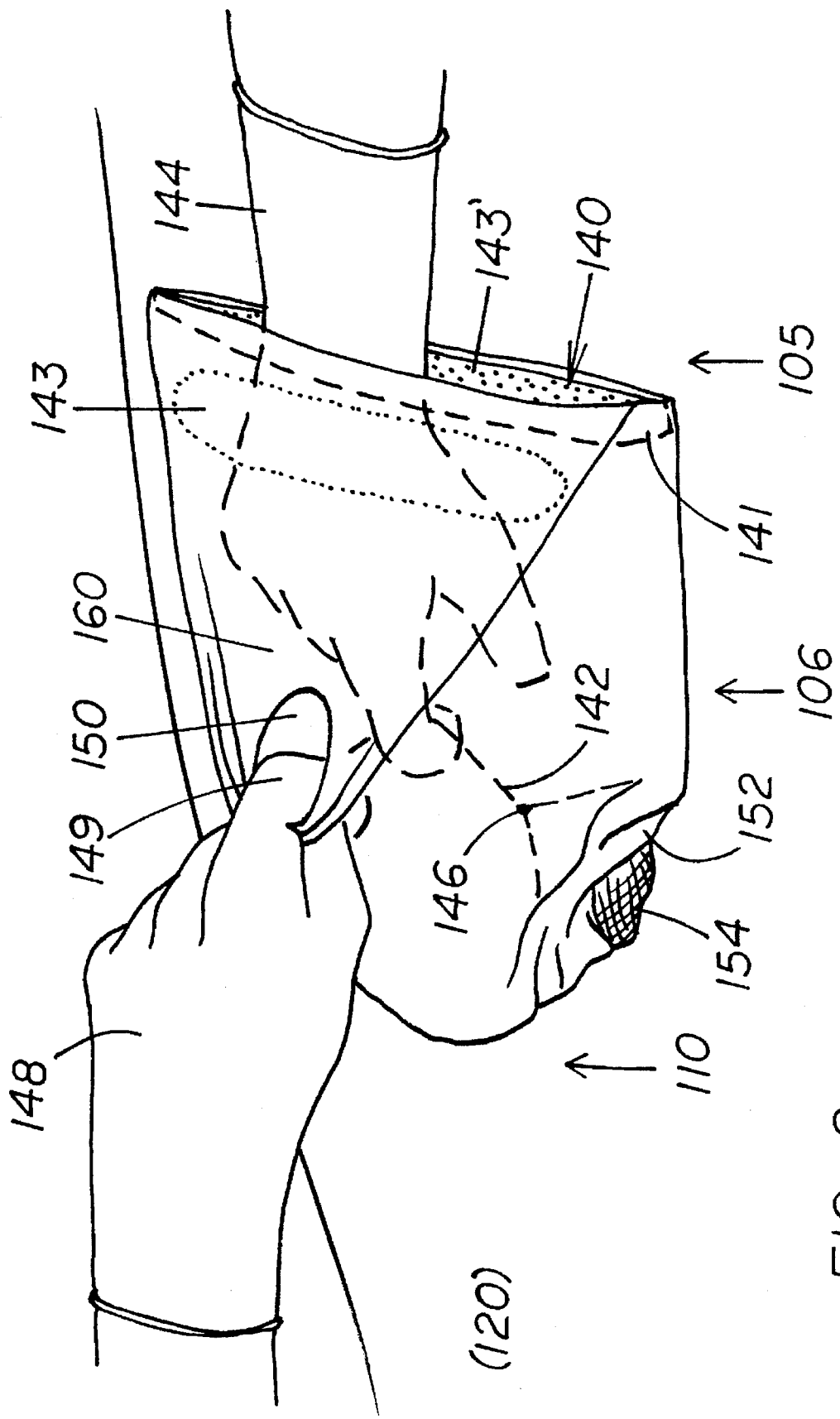
FIG. 2C is an oblique drawing of the invertible version of the bandage of FIG. 2B in the process of being inverted upon removal.

FIGS. 2A–2C show embodiments of the bandage which enable it to be turned inside out upon removal, thus causing surfaces once contacting a patient to be pulled into an internal cavity formed during the inversion process. This capability reduces exposure to harmful pathogens in several ways, including the ability to dispose the bandage as soon as practically possible upon its removal from the patient, and elimination of the need for separate disposal bags and containers, which might cause accidents during bandage transfer.

FIG. 2A shows one embodiment of an invertible bandage structure having an outer layer 30 which forms a pocket on the surface of the bandage facing away from the patient after application. The pocket has an opening or mouth 32 at its proximal end and, inside the pocket at its distal end 34 there is bonded, attached or sewn some form of grasping means used for the inversion process. In FIG. 2A, with a portion of the outer layer 30 removed as shown, this grasping means takes the form of a tab 36 which may be flexible or rigid and which may or may not include one or more holes 38 into which a finger may be inserted.

To invert the bandage of FIG. 2A, the individual removing the bandage inserts at least a portion of the hand, preferably the entire hand, into the opening 32 of the pocket, grabs the tab 36, which is preferably centrally attached with respect to the distal end 34, and pulls the tab 36 out through the mouth 32, thus inverting the structure. In this particular embodiment, the overall shape of the bandage may beneficially be tapered away from a more rectangular form shown in broken lines 31. Such a tapered structure should assist in helping the inversion process to commence in a smooth manner. Additional tapering, as indicated by broken lines 37, may likewise optionally be provided. Although the tapering indicated by 37 may actually slightly increase the difficulty in inverting the structure midway through the inversion process, such a tapering might result in a final structure which is much more easily sealed into its contained, final form. As mentioned previously, geometrical considerations such as the size, shape and tapering of the bandage, are all options which remain in keeping with this invention, depending upon the size of the bandage, its application, and so forth.

FIG. 2B illustrates in oblique form yet another alternative version of the invertible embodiment of the invention, in this case a bandage having an outer layer 50 which faces away from the patient when the bandage is applied, and a mouth formed on its proximal end. In contrast to the tab of FIG. 2A, however, the distal end has attached, sewn or otherwise bonded in its corners 58 a wire, cord or string 56. To remove this version of the bandage, a portion of the hand is inserted into the mouth 52 and the string 56 is grabbed with one or more fingers. One advantage of this configuration is that by pulling centrally on the string 56, the corners 58 naturally tend to move toward the center portion of the bandage proper, thus easing the inversion motion.

FIG. 2C shows, in oblique form, a bandage according to alternative 2B in the process of being inverted and removed from the patient 120. At its proximal end 105, the bandage includes an opening or mouth 140 into which at least a portion of an individual's hand is inserted. This opening 140 preferably including a flap 160 which may later be used to seal the bandage in its final inverted form. The flap preferably folds to an extent into the opening 140 at 141, thus advantageously creating a semi-rigid or substantially rigid edge along the top of the opening 140. Having the flap 160 initially folded into the mouth 140 prior to inversion assists in the inversion process, as does the rigidity resulting along the top edge of the opening 140.

The undesirable of the flap 160 as depicted in FIG. 2 preferably further includes an adhesive 143 which may serve various purposes. Prior to inversion, for example, this adhesive 143 may held to hold flap 160 down against the top surface of the upper layer forming the pocket. This adhesive action should not be too strong, however, since the flap 160 will need to release from this upper surface during the final stages of inversion. As such, a non-stick or reduced-tack surface may be provided directly beneath the adhesive 143 on the upper surface forming the top layer of the picket to ensure that a release is achieved.

Once the bandage is fully inverted, this adhesive 143 will be used to seal the bag upon closure. In order to ensure a sufficient seal, a second adhesive region 143' may be provided corresponding to that of 143 in the correct area upon inversion such that the flap may be folded over and pressed thereagainst. For example, adhesive 143 and its accompanying adhesive area 143' may both be of the contact adhesive variety. Various other techniques are possible for the sealing of the bandage however, including a separate piece of tape, a zip-lock type of structure, and so forth, as previously mentioned. The adhesive area 143' also serves to hold the opening 140 closed until needed, but this adhesive action should not be strong enough to confound easy entry into the pocket. It is when adhesive areas 143 and 143' are brought together, as per FIG. 3, that bonding of the two surfaces preferably be substantial.

At the distal end of the bandage 106 and internal to the pocket is some form of grasping means, in this case a string 142 attached at points 146 within the internal bandage structure, such as that depicted in FIG. 2B. The individual removing the bandage may thus grab the string 142 as shown with one or more fingers and pull in the direction of the pocket opening 140 to perform the inversion process. At the same time, as the one hand 144 of the individual inverting the bandage pulls on the string 142, the other hand 148 may conveniently grasp the distal end of the flap 160 with a finger 149 inserted through a hole 150 formed in the flap 160. As the string 142 is pulled, the internal distal ends 146 are pulled inwardly, so that the adhesive portion 152 and absorbent portion 154 are curled or otherwise deformed as the bandage is inverted these surfaces 152 and 154 being pulled into an inverted pouch created as the hands 144 and 148 are pulled apart from one another. Although the flap 160 is shown in generally triangular form with a rounded end other configurations are possible, and the number of holes 150 may be increased or decreased.

Figure 3:
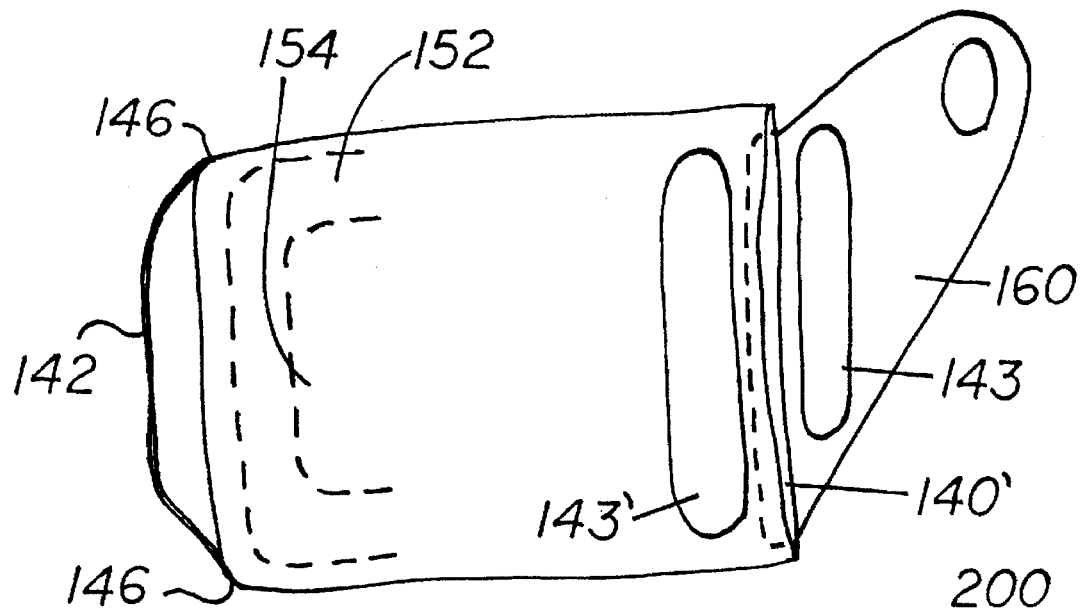
FIG. 3 is an oblique drawing of the invertible bandage in a final, inverted form.

FIG. 3 shows at 200 the bandage of FIG. 2C in its final inverted form. The string 142 will now be externally exposed and, indeed, may be used for convenient carrying. The flap 160 may now been folded over so as to seal the entrance through which the bandage was inverted. The broken lines 152 and 154 are used to indicate a portion of the patient contacting areas, which are now entirely enclosed within an internal cavity, with a new opening 140', formed through the inversion process. As seen in FIG. 3, the adhesive 143 on flap 160 may now be folded over so as to make contact with adhesive 143', thus sealing the inverted structure.

Figure 4:
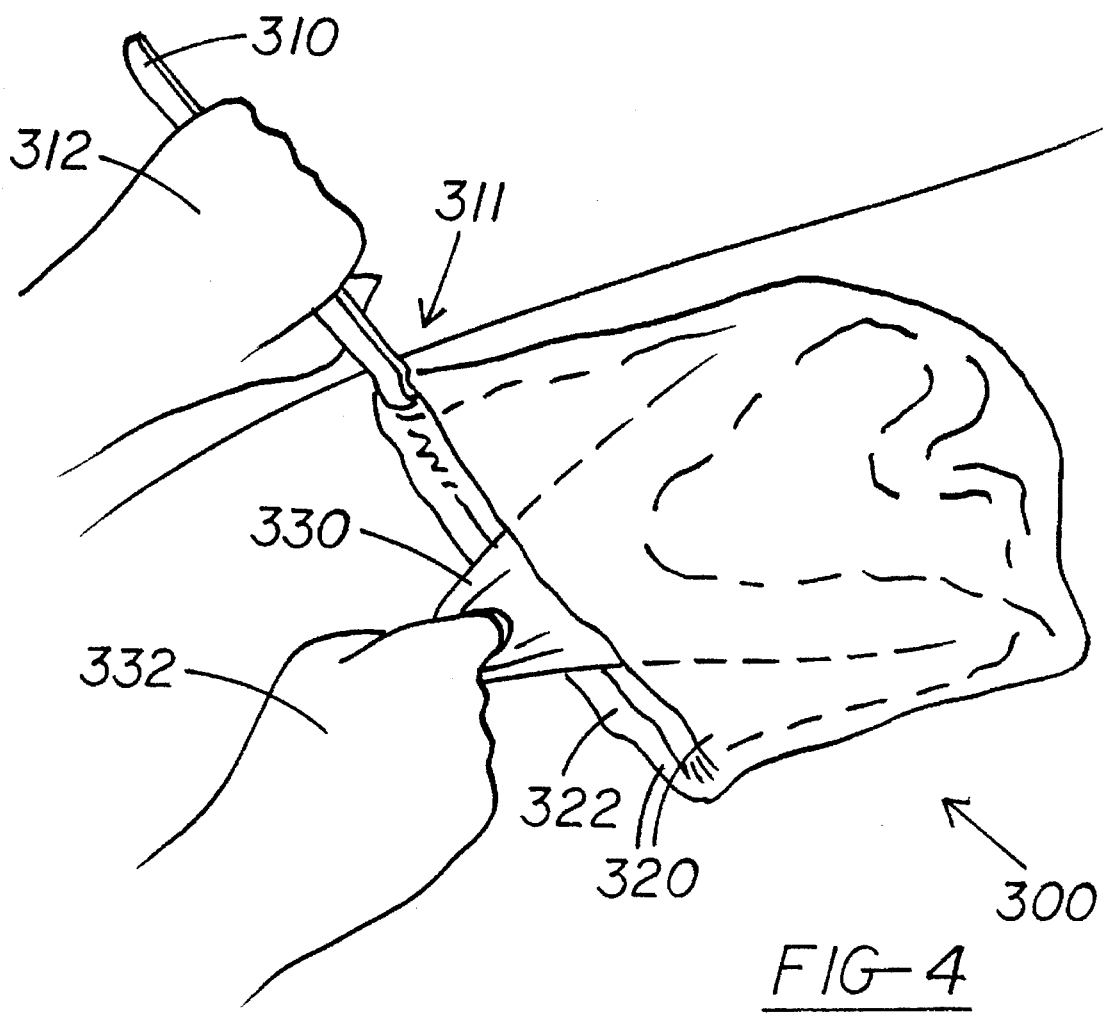
FIG. 4 illustrates an alternative embodiment of the invention including means for holding and stabilizing the opening of the pocket with one hand while performing the inversion operation with the other.

FIG. 4 illustrates the process of inverting yet a further alternative of the bandage, in this case including an optional protrusion in the form of a stick or bar 310 which may have a hinge 311 so that stick 310 may be used to seal the opening 322 prior to inversion and may additionally be folded back onto the opening of the inverted bandage to seal it in lieu of a flap or separate tape pieces. As shown, in operation, an individual removing the bandage 300 will grasp the stick 310 with a first hand 312 while grabbing the internal grasping means at the distal end of the bandage with his or her second hand 332. The grasping means in this case is a tab 330 having a hole to receive a finger of hand 332. In FIG. 3, the individual removing the bandage is partially through the process of inverting the same, such that the distal end of the bandage is now distorted as the tab 330 is being pulled between edges 320 which make up the opening 322. Edges 320 may further include embedded or external stiffening members (not visible in FIG. 4) which, in conjunction with the protruding stick 310, may alternatively further stabilize the opening 322 of the proximal end of the bandage until finally inverted. Stick 310 may be constructed and hinged in such a manner allowing it to be folded back over the open end to seal the internal cavity formed through the inversion process.

Figure 5:
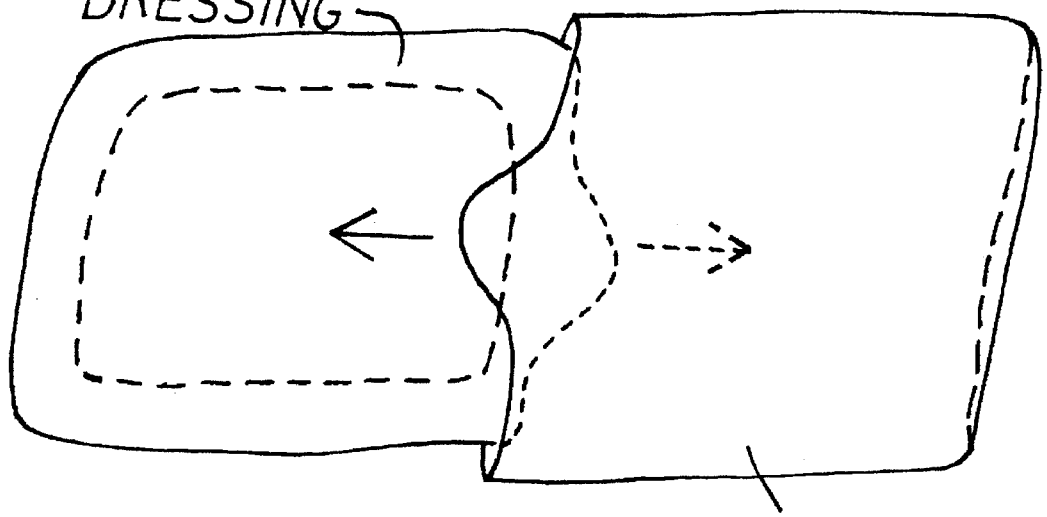
FIG. 5 is an oblique drawing of an alternative structure wherein the patient-contacting surface slider into an integral disposal pouch.

Broadly, in one embodiment, the present invention provides a composite structure for a bandage or wound dressing whereby a surface once contacting a patient may be subsequently contained in an integral disposal bag, pouch or cavity. Accordingly, it should be understood that numerous alternatives are possible beyond the invertible structures described and illustrated herein. One further alternative is shown in FIG. 5, where the patient-contacting layer slides into a disposal sleeve. Other possibilities include the folding and/or rolling up of the patient-contacting surface(s).

Having thus described my invention, I claim:

1. A composite wound dressing, comprising:

an absorbent pad having a patient-facing surface and a second surface facing away from the patient;

a non-stick layer covering the patient-facing surface of the absorbent pad; and a fluid-impermeable layer having a first surface which faces the patient and a second surface which faces away from the patient, the area of the fluid-impermeable layer being greater than that of the absorbent pad, the second surface of the absorbent pad being affixed to the first surface of the fluid-impermeable layer such that the fluid-impermeable layer extends beyond the area of the pad around at least a portion of its periphery, the first surface of the fluid-impermeable layer which extends beyond the periphery of the absorbent pad further including an adhesive layer for securement of the dressing directly to the patient.

2. The composite wound dressing of claim 1 wherein the adhesive layer covers the entire surface of the first surface of the fluid-impermeable layer, the adhesive of the layer being used both to affix the absorbent pad to the fluid-impermeable layer and to secure the dressing to the patient.

3. The composite wound dressing of claim 1, the means to turn the structure inside out including:

a pocket formed on the second surface of the fluid-impermeable layer, the pocket having an opening of dimensions sufficient to receive at least a portion of a human hand; and means for grasping disposed within the pocket whereby an individual may invert the dressing by pulling the grasping means out and through the pocket opening.

4. The composite wound dressing of claim 3, the means for grasping being a pull-string within the pocket.

5. The composite wound dressing of claim 3, further including stiffening means disposed around the opening of the pocket.

6. The composite wound dressing of claim 3, further including a rigid member protruding from the side of the dressing which an individual may grasp to stabilize the opening during inversion of the dressing.

7. The composite wound dressing of claim 3, the means for grasping being a pull-tab within the pocket.

8. The composite wound dressing of claim 7, the pull-tab including a finger-receiving aperture formed therethrough.

9. The composite wound dressing of claim 3, further including means to seal the dressing in the inverted form.

10. The composite wound dressing of claim 8, the means to seal the dressing including an integrated flap foldable over the opening to the pocket after the bandage has been inverted.

11. The composite wound dressing of claim 8, the means to seal the bandage including a plastic zipper-lock.

12. An invertible bandage, comprising:

a flattened structure having a proximal end and a distal end, the structure including a top surface and a bottom surface intended for contact with a portion of a patient's body and further including an adhesive layer on at least a portion of the periphery of said bottom for securement of the bandage directly to the patient, the bottom surface being covered at least partially with exposed absorbent material, the top surface having a pocket formed thereupon to receive a portion of the hand of an individual engaged in invertingly removing the bandage from the patient, the pocket having a mouth located at its proximal end and grasping means disposed within the pocket at its distal end, whereby the individual may grasp the grasping means and pull the bandage inside out to create an inverted form with the absorbent material no longer exposed but contained within an internal cavity formed upon insertion.

13. The invertible safety bandage of claim 12, further including means to seal the structure in its inverted form.

* * * * *

UNITED STATES PATENT AND TRADEMARK OFFICE
CERTIFICATE OF CORRECTION

PATENT NO.   : 5,643,189
DATED        : July 1, 1997
INVENTOR(S)  : Michael A. Masini It is certified that error appears in the above-indentified patent and that said Letters Patent is hereby corrected as shown below:

Column 4, line 55:   Replace "undesirable" with --underside--.

Column 4, line 64:   Replace "picket" with --pocket--.

Column 6, line 32:   Replace "patient." with --patient, said dressing further including means to turn the dressing inside out upon removal to create an inverted form wherein the surfaces once contacting the patient are no longer externally exposed.--

Column 7, line 6:   Replace "bottom for" with --bottom surface for--.

Signed and Sealed this

Twenty-eighth Day of October, 1997

Attest:

BRUCE LEHMAN

Attesting Officer    Commissioner of Patents and Trademarks